(12) United States Patent
Lee et al.

(10) Patent No.: US 9,630,122 B2
(45) Date of Patent: *Apr. 25, 2017

(54) SALT REMOVAL AND TRANSPORT SYSTEM AND METHOD FOR USE IN A MONO ETHYLENE GLYCOL RECLAMATION PROCESS

(71) Applicant: Cameron Solutions, Inc., Houston, TX (US)

(72) Inventors: Joseph Min-Hsiun Lee, Houston, TX (US); Gary W. Sams, Spring, TX (US)

(73) Assignee: Cameron Solutions, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/056,256

(22) Filed: Feb. 29, 2016

(65) Prior Publication Data

US 2016/0175732 A1 Jun. 23, 2016

Related U.S. Application Data

(63) Continuation of application No. 14/307,232, filed on Jun. 17, 2014, now Pat. No. 9,272,972.

(51) Int. Cl.
*C07C 29/80* (2006.01)
*C07C 29/76* (2006.01)
*B01D 1/30* (2006.01)
*C07C 31/20* (2006.01)

(52) U.S. Cl.
CPC .............. *B01D 1/30* (2013.01); *C07C 29/76* (2013.01); *C07C 29/80* (2013.01)

(58) Field of Classification Search
CPC ....... C07C 29/76; C07C 29/80; C07C 31/202; B01D 3/06; B01D 21/267; B01D 3/143
USPC .......................................................... 210/723
See application file for complete search history.

(56) References Cited

U.S. PATENT DOCUMENTS

2013/0118989 A1 5/2013 Fernandez

FOREIGN PATENT DOCUMENTS

| WO | 2007073204 | 6/2007 |
|---|---|---|
| WO | 2009017971 | 2/2009 |
| WO | 2010080038 | 7/2010 |
| WO | 2013074183 | 5/2013 |

OTHER PUBLICATIONS

Cameron: "Puremeg-Meg Reclamation and Regeneration Technology", Jan. 1, 2013.

*Primary Examiner* — Jafar Parsa
(74) *Attorney, Agent, or Firm* — Gable Gotwals

(57) ABSTRACT

A system for removing salt from a process stream being fed into a flash separator introduces a swirling motive fluid into the fluid column of the separator. The swirling motive fluid comes into contact with salt components residing in the fluid of the column to create a salt slurry. Means to limit the upward movement of the swirling motive fluid can be provided. The salt slurry is then removed and can be sent to a brine generation vessel. Saturated brine from the vessel is transported back to the fluid column to replace the motive fluid in the column.

5 Claims, 3 Drawing Sheets

SALT REMOVAL AND TRANSPORT SYSTEM AND METHOD FOR USE IN A MONO ETHYLENE GLYCOL RECLAMATION PROCESS

CROSS-REFERENCE TO RELATED APPLICATIONS

This application is a continuation application which claims priority to U.S. patent application Ser. No. 14/307,232 filed on Jun. 17, 2014, which is incorporated herein by reference.

BACKGROUND OF THE INVENTION

This invention relates to processes designed to treat mono ethylene glycol (MEG) used in the oil and gas industry, especially in offshore locations, to control hydrates formation. More particularly, the invention relates to MEG reclamation processes which are designed to remove salts and other contaminants from a wet MEG feed stream.

In the oil and gas industry, dry (lean) MEG is used to control the formation of hydrates within the produced stream. The now wet (rich) MEG is, in turn, dried by way of a MEG reclamation process so the MEG can be used again in hydrate control.

The unit used to recover MEG usually includes three sections: pre-treatment, flash separation, and MEG regeneration. Those sections can be followed by salt management and calcium removal sections.

In the pre-treatment stage, the rich MEG containing some dissolved gas and hydrocarbon liquids must pass through a three-phase separator vessel. The gas is flashed and recovered hydrocarbon liquids are sent to the production separator. The rich MEG is sent to a flash separator. The rich MEG stream comprised of produced water and MEG is fed to the flash separator where it is brought into contact with a hot recycle stream of MEG. The flash separator operates under vacuum. The MEG and water components of the rich MEG stream are flashed and exit through the top of the flash separator where they are sent to the MEG distillation column for regeneration. The salt components of the rich MEG stream precipitate in the flash separator.

The MEG regeneration section is a refluxed distillation column. The distillation column also operates under vacuum and distills the water from the MEG-water vapors coming off the top of the flash separator. Salt-free, lean MEG produced at the bottom of the distillation column is pumped to storage for reuse. The vaporized water passes overhead from the distillation column. The water is condensed and collected in the reflux drum. A small amount is returned to the distillation column as reflux, and the remaining is routed to treatment.

The salt crystals that precipitate in the flash separator are separated by gravity to the bottom of the brine column, where they are transferred to the salt tank. There, the salts are concentrated before removal through a centrifuge.

The salts in produced water cover a variety of species, but generally are categorized into monovalent salts (typically sodium and potassium), and divalent salts (typically calcium and magnesium). The divalent salts cannot be effectively precipitated in the same manner as the monovalent salts, so a separate calcium removal process may be installed. Effective calcium control is accomplished as the divalent salts are collected, reacted and removed through a centrifuge with the centrate overflow returning to the process.

Current methods of removing the salt crystals from bottom of the brine column involves a lot of equipment, including but not limited to complicated and expensive centrifugal filters or desanding cyclones, centrifuge pump filtration systems, a salt tank, a centrate tank, and a density measurement device. Reducing the footprint of the system required to remove the salt crystals is important for making more efficient use of space, reducing off-shore construction costs, and increasing ease of system operation and maintenance.

SUMMARY OF THE INVENTION

A system for removing salt from a rich mono ethylene glycol ("MEG") stream being fed into a flash separator includes means for isolating or limiting an upward movement of the fluid residing in the brine (fluid) or downcomer column of the separator from the MEG, a solids fluidization device having means for causing a motive fluid to swirl when exiting the device; means for removing a salt slurry created by the swirling motive fluid.

The isolating means is preferably an on-off valve located between a top and a bottom end of the brine column of the flash separator, the on-off valve when in the off position isolating the fluid residing in the brine column above the valve from the fluid residing and below the valve. A butterfly-type valve is an adequate on-off valve.

The solids fluidization device is located within the brine column and below the on-off valve and has means that cause the motive fluid entering the device to swirl when exiting the device. The swirling motive fluid then comes into contact with salt components residing in the resident fluid isolated below the on-off valve. The motive fluid can be a produced water stream, a condensate water stream, or a stream that is some combination of the two. The swirling flow (e.g., vertiginous, rotary, or cyclonic) creates a salt slurry which is removed from the brine column by the removal means and passed to a brine generation vessel.

The causing means is preferably a device having a plurality of slots located toward an upper end of the solids fluidization device and arranged tangential to, surrounding, and in communication with a central inner bore of the device. The removal means is preferably a slurry delivery head located in the brine column and directly above the solids fluidization device.

The system further includes a brine generation vessel arranged to receive the salt slurry from the brine column. The brine generation vessel provides a saturated brine which can be transported back into the brine column and replace the motive fluid which was introduced earlier.

A method of removing salt from a rich MEG stream being fed into a flash separator includes the steps of:
i. isolating fluid containing solid/salt already residing toward a lower end of the brine column from MEG residing toward an upper end of the brine column;
ii. introducing a swirling motive fluid stream into a bottom end of the brine column to form a salt slurry stream; and
iii. removing the salt slurry stream.

The isolating step is preferably done by way of an on-off valve, which could be a butterfly-type valve. The introducing step is preferably by way of a solids fluidization device having a plurality of spaced-apart vertical slots arranged tangential to, surrounding, and in communication with a central inner bore of the device. The removal step is by way of a slurry delivery head located above the solids fluidization device. After the step iii, a saturated brine stream can be introduced into the brine column as a way to displace the motive fluid. After the saturated brine stream is introduced into the column, the valve can be opened and the isolated fluids can be allowed to come into contact with one another again.

The objectives of this invention are to (1) eliminate the need for complicated and expensive centrifugal filters and desanding hydrocyclones to remove salt; (2) eliminate the need for centrifuge filtration, a salt tank, a centrate tank, and density measurement devices; and (3) require less foot print than the prior art systems and methods and have lower construction costs and be easier to operate and maintain than those prior art systems and methods.

ELEMENTS AND NUMBERING USED IN THE DRAWINGS

| | |
|---|---|
| 10 | Salt transport system |
| 20 | Flash separator |
| 21 | Upper end |
| 25 | Rich (wet) MEG stream |
| 27 | Water and MEG vapor stream |
| 29 | Brine (fluid) or downcomer column or section |
| 31 | MEG/brine transition zone |
| 33 | On-off valve |
| 35 | Recycle loop |
| 37 | Bottom or lower end of 29 |
| 39 | Upper end of 29 |
| 40 | Sand removal device |
| 41 | Inlet |
| 43 | Upper end of 40 |
| 45 | Slots |
| 47 | Inner bore |
| 49 | Produced or condensate (carrier or motive) water stream |
| 51 | Swirling motive fluid stream |
| 53 | Salt slurry stream |
| 55 | Removal device or slurry discharge head |
| 60 | Brine generation vessel |
| 61 | Agitator |
| 63 | Brine stream |
| 65 | Salt slurry (discharge) stream |

DETAILED DESCRIPTION OF THE PREFERRED EMBODIMENTS

Figure 1:
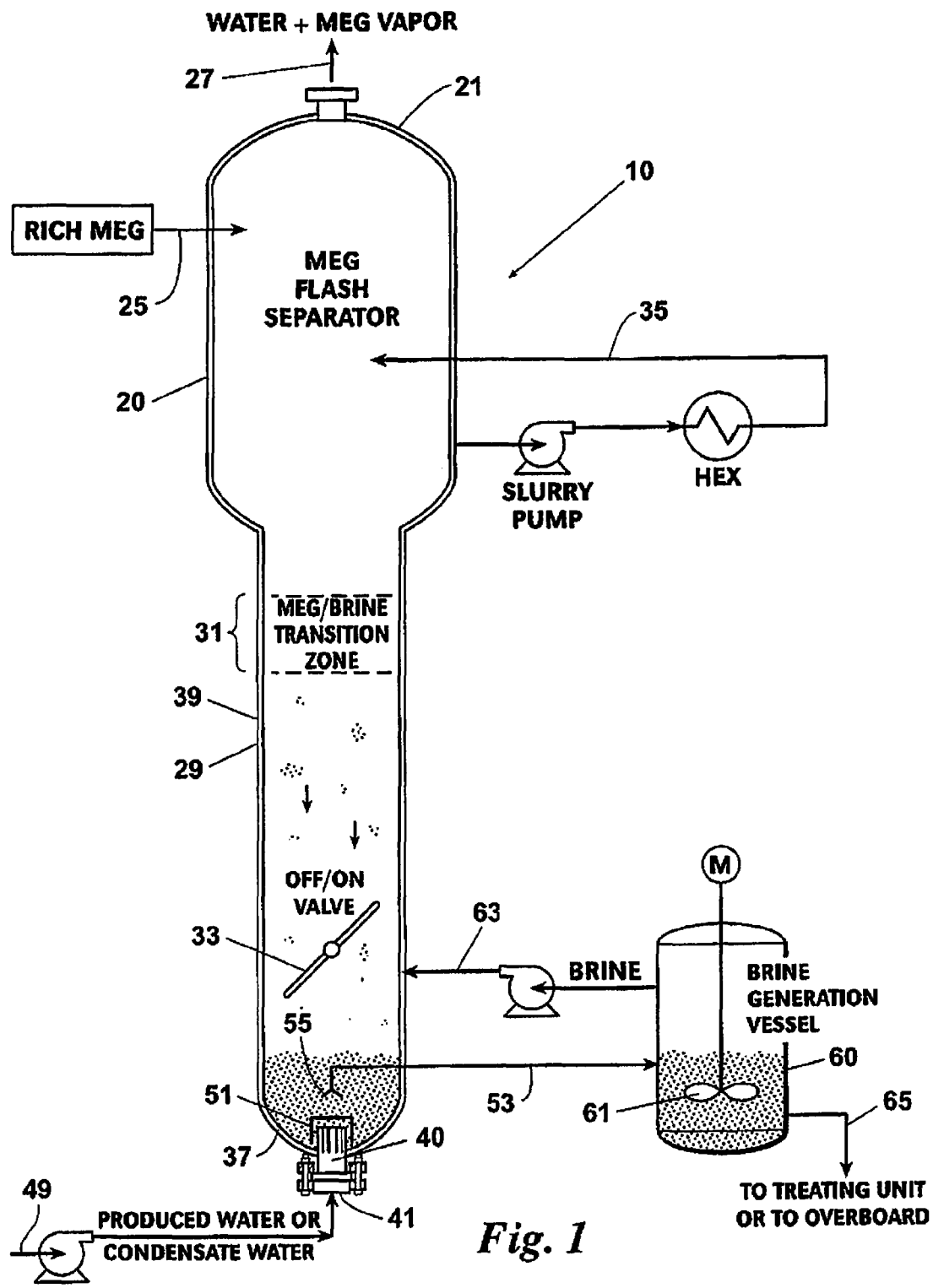
FIG. 1 is a schematic of a preferred embodiment of a salt transport system for a MEG reclamation or recovery process. The system includes a solids fluidization device located at the bottom end of the brine column of a flash separator and an on-off valve located between the fluidization device and the MEG/brine transition zone of the flash separator.
Figure 3:
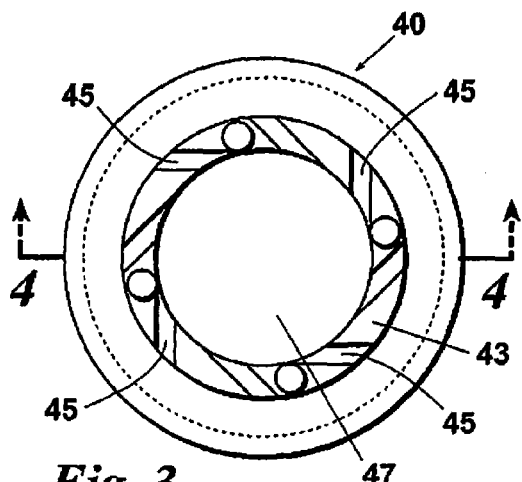
FIG. 3 is top view of the solids fluidization device of FIG. 2.
Figure 5:
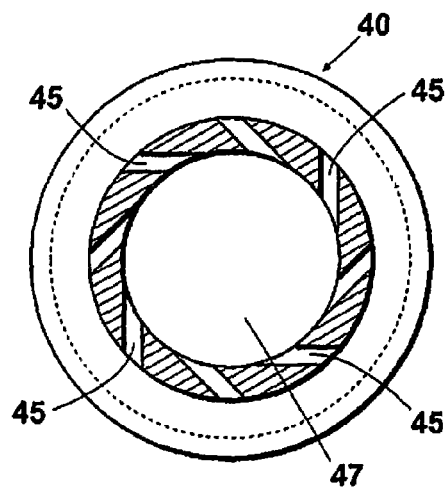
FIG. 5 is a cross-section view of the solids fluidization device of FIG. 2 taken along section line 5-5 of FIG. 2.
Figure 2:
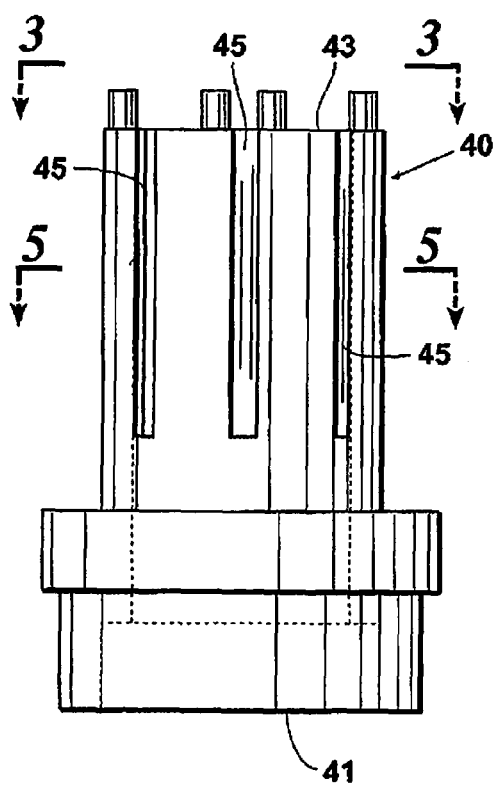
FIG. 2 is a front elevation view of a preferred embodiment of the solids fluidization device of FIG. 1.
Figure 4:
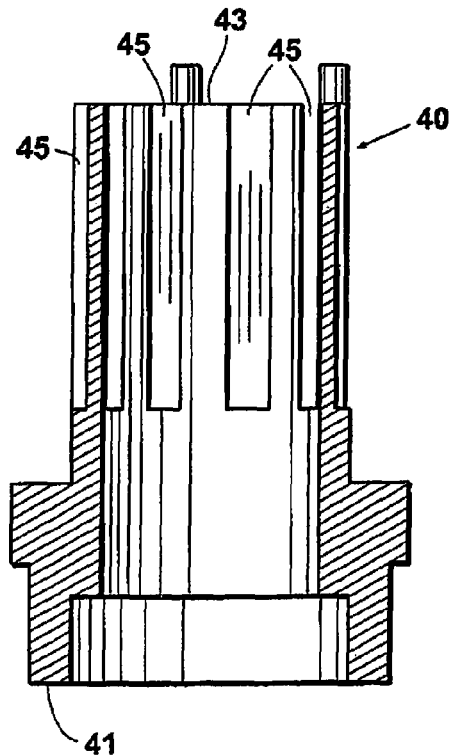
FIG. 4 is a cross-section view of the solids fluidization device of FIG. 2.
Figure 6:
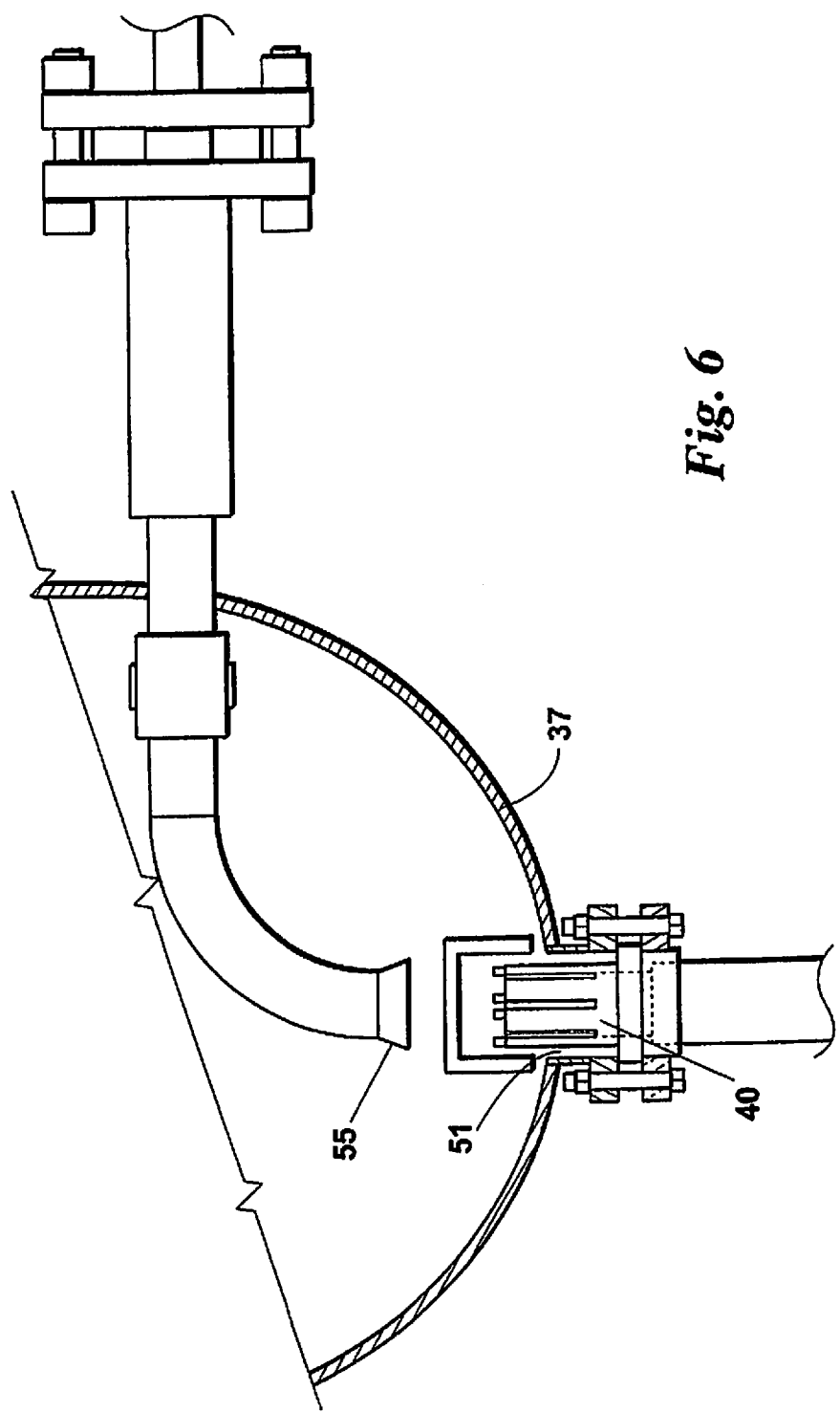
FIG. 6 is an enlarged view of the solids fluidization device of FIG. 1 and the removal device located directly above the solids fluidization device.

Referring first to FIGS. 1 and 6, a preferred embodiment of a salt transport system 10 for a MEG recovery or reclamation process includes a flash separator 20 having a solids fluidization device 40 located at the bottom end 37 of the brine or downcomer column 29 and an on-off valve 33 located between the device 40 and the MEG/brine transition zone 31.

The flash separator 20 is of a kind well known in the art. In the separator 20 a rich (wet) MEG inlet stream 25 is brought into contact with a hot MEG recycle stream 35. The MEG and water components of the rich MEG stream 25 are flashed and exit the upper end 21 of the separator 20 as a water and MEG vapor stream 27. The salt components of the rich MEG inlet stream 25 precipitate in the brine (fluid) column 29 of the separator 20. A MEG/brine transition zone 31 forms in the column 29 between the MEG and the brine.

Solids fluidization device 40 is arranged at the bottom end 37 of the column 29. The device 40 includes means which produce or cause a swirling (e.g. vertiginous, rotary or cyclonic) motion or flow 51 of the motive fluid as it exits device 40. One suitable device 40 is a HYDROTRANS™ solids fluidization and removal device (Cameron Process Systems, Houston, Tex.). Any other device may be used as the fluidization device provided the device creates a swirling (e.g., vertiginous, rotating, or cyclonic) motive fluid flow when the flow exits the device.

Referring to FIGS. 2-5, the HYDROTRANS™ device includes a plurality of spaced-apart slots 45 arranged tangential to, surrounding, and in communication with an inner bore 47 which receives a motive fluid stream 49 at the lower inlet end 41 of the device. Motive fluid steam 49—which can be a produced water or condensate water stream (or some combination thereof)—exits the slots 45 of device 40 as a swirling motive fluid stream 51. The swirling motion of the motive fluid stream 51 mixes with the fluid containing solid/salt already residing in the column 29 to fluidize the salt components, thereby creating a salt slurry stream 53. By way of example, during the first five minutes of operation, the concentration of salt in the device 40 can be about 20 vol % on average.

Unlike a desanding hydrocyclone—which produce a cyclonic flow within the device but a straight over- and underflow exiting the device (i.e., straight in, cyclonic within, and straight out)—the solids fluidization device 40 produces this type of flow external to the device (i.e., straight in and rotary or cyclonic out).

The removal device 55, which can be a slurry discharge head, resides just above the upper end 43 of solids fluidization device 40. Removal device 55 carries the salt slurry stream 53 to a brine generation tank or vessel 60.

Because the brine in the column 29 is saturated with salt, adding produced water to it causes the lower density (not saturated) produced water 49 to flow to the upper end 39 of the column 29 and MEG to flow to the bottom end 37. This causes MEG loss. To prevent this loss from occurring, system 10 limits upward movement of the fluid, which can be by way of isolation means such as on-off valve 33, which may be a butterfly-type valve. When the valve 33 is in the off or closed position, it prevents the produced water from flowing to the upper end 39 of the column 29. The valve 33 isolates the fluid or brine located above and below the valve 33 from one another.

Once the salts are removed from the bottom end 37 of the column 29, the saturated brine in the brine generation vessel 60 is pumped back to the column 29 below the on-off valve 33 to replace the produced water. Once the produced water is replaced with the saturated brine, the on-off valve 33 is put in the on or open position to allow the salt to settle below the valve 33 and into the bottom 37 of column 29.

If a 1" HYDROTRANS is used as device 40, a flow rate of 4 m³/hr is required to remove the salt from the bottom end 37. For about the first five minutes of operation, about 0.33 m³ of a salt slurry stream 53 (about 20 vol %) to the brine generation vessel 60. Assuming a void space of 40% between the salt particles (i.e., the salt represents 60%), the total amount of salt removed in five minutes (0.083 hr) is 0.04 m³ (4 m³/hr×0.083 hr×0.2×0.6). The salt density is 2,165 kg/m³. Therefore, the amount of salt removed in five minutes of operation (i.e., with the valve 33 closed) is about 87 kg. If the amount of salt settled at the bottom end 37 is higher (or lower) than in the example, the removal process can be adjusted accordingly.

System 10 does not require any centrifugal filters or desanding cyclones to remove salt from the brine column 29, nor does it require centrifugal filtration, salt and centrate tanks, and density measurement devices. System 10 also requires less foot print than the prior art systems and methods, has lower construction costs, and is easier to operate and maintain.

After the salt removal process is completed, an agitator 61 can be used to agitate and dissolve the salt in the liquid phase within the brine generation vessel 60. The saturated brine solution can then be pumped as a saturated brine stream 63 to the column 29 to replace the produced water. Once this operation is complete, the valve 33 can be put in the on or open position to accumulate salt in the bottom end 37 of the column 29.

When the brine generation vessel 60 is filled with enough salt, agitator 60 will again be turned on to make a salt slurry stream 65 which is pumped to a water treating unit (not shown) or to overboard (if allowed).

A method of removing salt from a rich MEG stream which makes use of system 10 includes the steps of:
 i. isolating fluid in the brine column 29 of the flash separator 20 by closing a valve 33 located above the bottom end 37 of the brine column 29 and below the upper end 39 of the column 29;
 ii. introducing a swirling motive fluid stream 51 into the bottom end 37 of the brine column 29, the swirling motive fluid stream 51 coming into contact with salt components residing in the column 29 and forming a salt slurry stream 53;
 iii. removing the salt slurry stream 53 from the brine column 29 to a brine generation vessel 60;
 iv. agitating the contents of the brine generation vessel 60 to form a saturated brine 63;
 v. transferring the saturated brine 63 back to the column 29; and
 vi. opening the valve 33 after step v is completed.

Salt removal system 10 and the method for its use is an improvement over prior art systems and methods. The prior art makes use of complicated and expensive centrifugal filters or desanding cyclones to remove salt from the brine column 29 of the flash separator 20 along with centrifuge filtration, a salt tank, a centrate tank, and density measurement devices.

While preferred embodiments of system 10 and a method for its use have been described in detail, the scope of the invention is defined by the following claims.

What is claimed:
1. A method of fluidizing salts to aid salts removal, the method comprising the steps of:
 i. introducing a swirling motive fluid into a bottom end of a fluid column of a flash separator, the swirling motive fluid contacting salt components of a fluid residing in the fluid column;
 ii. limiting an upward movement of the swirling motive fluid within the fluid column; and
 iii. removing a salt slurry produced by the swirling motive fluid.
2. A method according to claim 1 wherein the limiting step is by way of a valve located in the fluid column.
3. A method according to claim 1 further comprising the step of recirculating the salt slurry to the fluid column.
4. A method according to claim 1 further comprising the step of introducing, after the step ii, a saturated brine stream into the fluid column.
5. A method according to claim 1 wherein a source of the swirling motive fluid is at least one of a produced water stream and a condensate water stream.

* * * * *